(12) United States Patent
Brunnett et al.

(10) Patent No.: US 7,010,081 B2
(45) Date of Patent: Mar. 7, 2006

(54) TAPERED ROLLER BEARING

(75) Inventors: William C. Brunnett, Concord, OH (US); Ronald B. Sharpless, Cleveland, OH (US)

(73) Assignee: Koninklijke Philips Electroncis N.V., Eindhoven (NL)

( * ) Notice: Subject to any disclaimer, the term of this patent is extended or adjusted under 35 U.S.C. 154(b) by 148 days.

(21) Appl. No.: 10/255,927

(22) Filed: Sep. 26, 2002

(65) Prior Publication Data

US 2004/0062343 A1 Apr. 1, 2004

(51) Int. Cl.
*A61B 6/00* (2006.01)

(52) U.S. Cl. ............................................. 378/15; 378/4
(58) Field of Classification Search .................. 378/15, 378/17, 193–198, 132, 125, 4, 144; 384/116, 384/279, 446, 107, 126–128; 310/90, 90.5
See application file for complete search history.

(56) References Cited

U.S. PATENT DOCUMENTS

| | | | |
|---|---|---|---|
| 4,232,914 A | * 11/1980 | Bowen, III | 384/567 |
| 4,651,007 A | 3/1987 | Perusek et al. | 250/363 |
| 5,473,657 A | * 12/1995 | McKenna | 378/4 |
| 5,784,428 A | 7/1998 | Schmidt | 378/4 |
| 5,982,844 A | * 11/1999 | Tybinkowski et al. | 378/4 |
| 6,022,325 A | 2/2000 | Siczek et al. | 600/568 |
| 6,204,577 B1 | * 3/2001 | Chottiner et al. | 310/42 |
| 6,337,894 B1 | 1/2002 | Tybinkowski et al. | 378/4 |

FOREIGN PATENT DOCUMENTS

EP          1 095 620          5/2001

* cited by examiner

*Primary Examiner*—Edward J. Glick
*Assistant Examiner*—Elizabeth Keaney
(74) *Attorney, Agent, or Firm*—Fay, Sharpe, Fagan, Minnich & McKee LLP

(57) ABSTRACT

In a diagnostic system, having a rotating gantry (24) and a stationary gantry (22), a bearing race (50) rotates with surface portions having varying linear velocities in accordance with distance from an axis (A) of rotation. Tapered roller bearings (46) interface the bearing race (50) and are conically shaped to velocity match the variable linear surface velocity race (50). The race (50) preferably includes two faces, which provide both axial and radial supporting surfaces for the bearings (46) to interface. The bearings (46) are disposed about the race (50) in pairs. A drive motor (52) is connected to one of the bearings (46) to rotate the gantry (24).

18 Claims, 5 Drawing Sheets

TAPERED ROLLER BEARING

BACKGROUND OF THE INVENTION

The present invention relates to medical imaging arts. In particular, it relates to a rotating gantry such as those found in $3^{rd}$ and $4^{th}$ generation CT scanners, and will be described with particular reference thereto. However, the invention will also find application in conjunction with nuclear cameras and other imaging systems with rotating bearings, and is not limited to the aforementioned application.

Typically, $3^{rd}$ and $4^{th}$ generation CT systems have rotating gantries and stationary gantries. The two gantries are interfaced by a bearing system that allows rotation of the first gantry relative to the second gantry.

A large ball bearing assembly, often a meter or more in diameter, has been used to provide the interface between the gantries. Large ball bearing assemblies are expensive and tend to be noisy.

In other systems, roller bearings have been used. Cylindrical rollers support the rotating gantry in both axial and radial directions. Typically, the rotating gantry has three bearing races, or tracks along which the bearings roll. A circumferential race allows the bearings to give the rotating gantry radial support (a normal force counteracting the force of gravity) while the second and third races allow bearings to give the rotating gantry lateral, that is, axial support. To prevent the rotating gantry from wobbling, the roller bearings press against the second and third races with significant opposing pressure.

While the gantry rotates with a constant angular velocity, portions of the gantry move with different radially dependent linear velocities. More specifically, portions of the second and third races more distant from the rotational axis of the gantry have a higher linear velocity than portions closer to the rotational axis. Stated differently, the linear velocity of any moving element is a function of radial position, as well as angular velocity of the gantry.

This is significant to, among other things, the second and third axial support bearing races. The outer edges of these two races move faster than the inner edges of the same races. Each cylindrical roller bearing that contacts the second and third races only rotate at a single speed. Thus, slippage occurs between the bearing races and the roller bearings, causing high friction and wearing both the bearing races and the bearings prematurely. Additionally, functional speeds of the gantry are limited, in order to balance the speed of the gantry and the wear that higher speeds incur on the races and the bearings.

The present invention contemplates an improved apparatus and method, which overcomes the aforementioned limitations and others.

SUMMARY OF THE INVENTION

According to one aspect of the present invention, a diagnostic imaging device is provided. First and second gantries are interfaced by a plurality of tapered roller bearings that provide support for the second gantry as it rotates. The bearings interface bearing races on the rotating gantry.

According to another aspect of the present invention, a method of diagnostic imaging is provided. A first, rotating gantry is supported with a plurality of tapered roller bearings attached to a second gantry. The first gantry is rotated concurrently with the roller bearings, races of the gantry being in contact with the roller bearings.

According to another aspect of the present invention, a roller bearing for use in conjunction with a computed tomography scanner is provided. The bearing includes an axle, a tapered conical body with a trapezoidal cross-section, the tapered side of the body being a contact surface of the bearing. A taper angle $\phi$ of the bearing is defined by $$\phi = \arcsin\left(\frac{d_o - d_i}{2L_c}\right)$$

where $d_o$ is the outer diameter of the bearing, $d_i$ is the inner diameter of the bearing, and $L_c$ is the length measured along an edge of the bearing. A polyurethane coating covers the bearing body.

One advantage of the present invention resides in increased life of the roller bearings and bearing races.

Another advantage resides in a reduced total number of roller bearings required.

Another advantage is that rotating friction of the bearing system is reduced.

Another advantage is that a single size of roller bearing can be used.

Another advantage resides in fewer precision machined bearing races.

Another advantage resides in a smaller rotating gantry.

Another advantage resides in an integrated drive motor.

Another advantage resides in reduced cost over similar systems currently in production.

Yet another advantage resides in faster rotational speeds.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

DETAILED DESCRIPTION OF THE PREFERRED EMBODIMENTS

Figure 1:
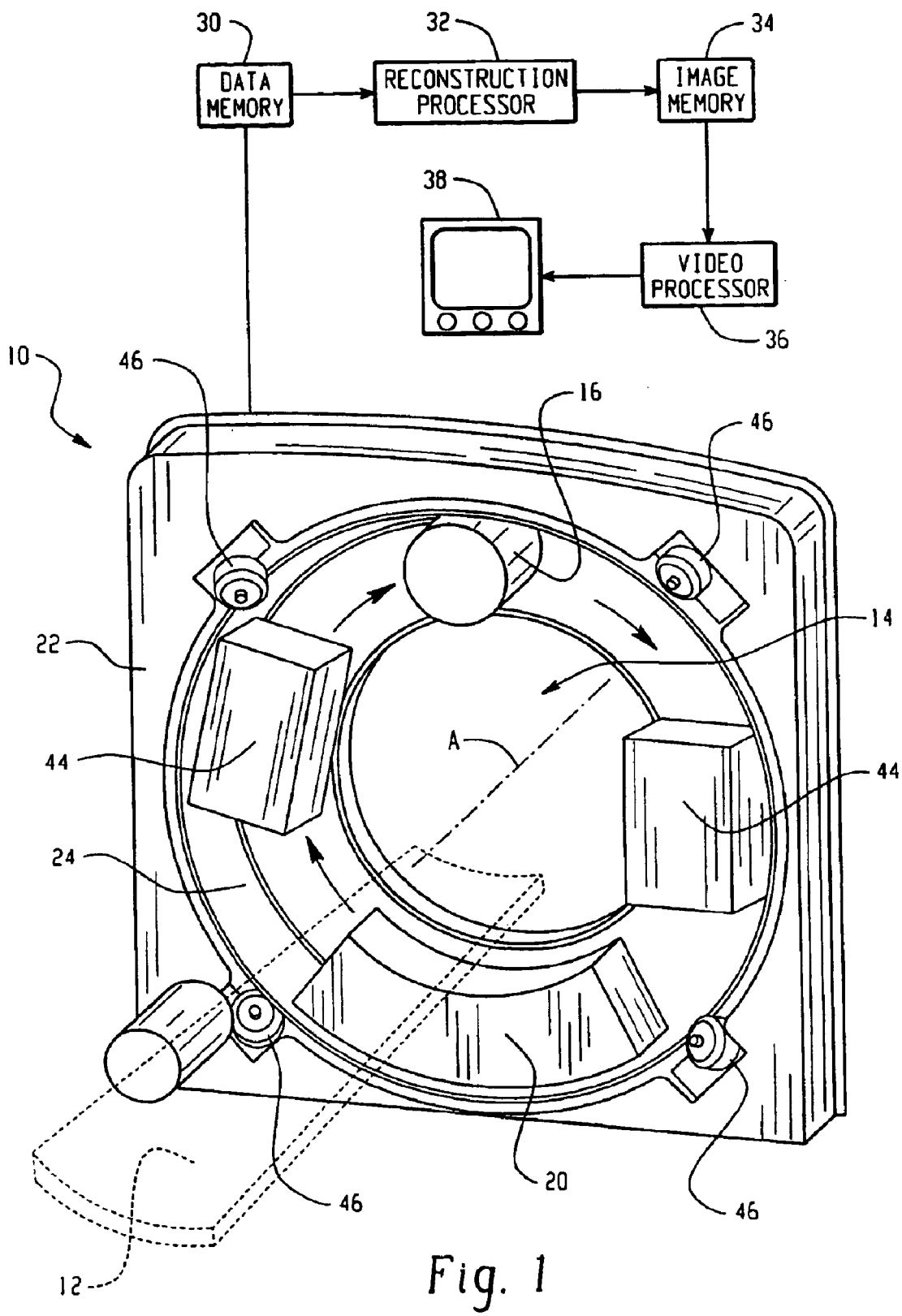
FIG. 1 is a diagrammatic illustration of a computed tomography scanner, in accordance with the present invention.

With reference to FIG. 1, a CT scanner 10 includes a subject couch 12 for moving a subject disposed thereon into and out of an imaging region 14. X-rays from an x-ray source 16 are shaped and collimated into a fan beam, pass through the imaging region 14 and are detected by a detector assembly 20 on the far side of the imaging region 14. In the illustrated $3^{rd}$ generation embodiment, the source 16 rotates concurrently with the detector assembly 20, always remaining 180° around the imaging region 14 from the detector assembly 20 as it rotates around an axis A. Alternately, a stationary ring of individual detectors on the stationary gantry 22 can replace the detector array 20, as in a 4$^{th}$ generation CT scanner.

Intensities of detected x-rays are collected in a data memory 30 as a rotating gantry 24 rotates about the subject. As the data is collected, a reconstruction processor 32 applies a convolution and backprojection algorithm, or other suitable reconstruction technique, to the collected data, forming an image representation. The image representation(s) are stored in an image memory 34. A video processor 36 withdraws selected portions of the image representations and formats them for viewing on a human readable monitor 38 such as a CRT monitor, active matrix monitor, LCD display, or the like.

The first, rotating gantry 24 is disposed within the second, stationary gantry 22. The x-ray source 16 and the detector array 20 are mounted on the rotating gantry 24 along with other associated electronics 44, such as power supplies, data buffers, etc.

The rotating gantry 24 is supported within the stationary gantry 22 by a plurality of tapered roller bearings 46. In the preferred embodiment, there are four sets of two bearings, making eight roller bearings total. Of course, the number of bearing pairs can be more or less, dependent upon other factors such as the weight of the gantry 24, functional speeds, and the like. Each bearing 46 rotates freely about its own bearing axle, the axle being mechanically fastened to the stationary gantry 22.

Figure 2:
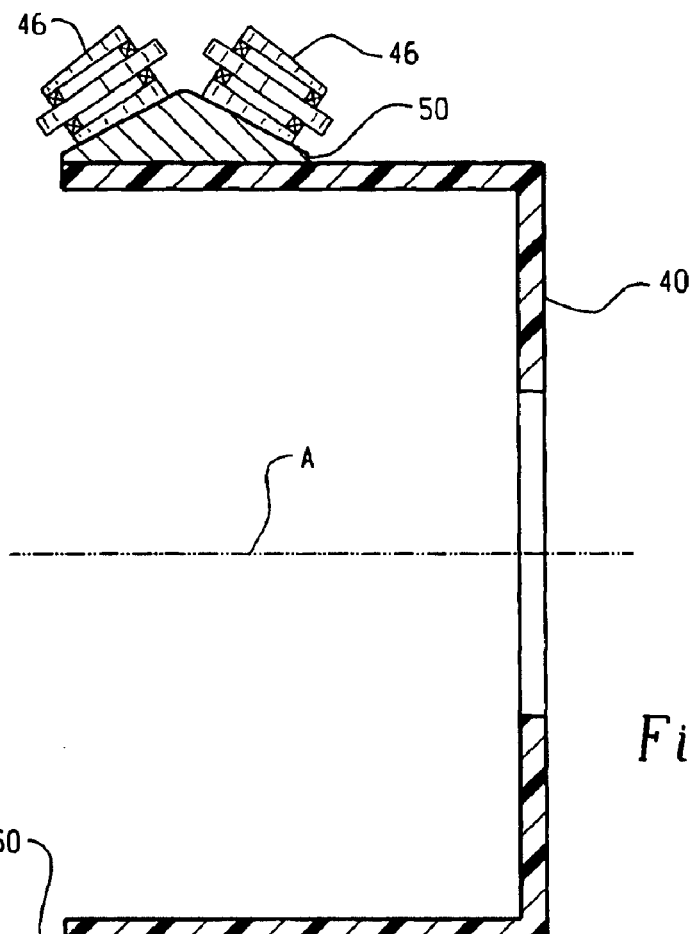
FIG. 2 is a cross-sectional view of the rotating gantry of FIG. 1 and tapered roller bearings, in accordance with the present invention.

With reference to FIG. 2, the bearings 46 interface with a conical bearing race 50, The race 50, depicted attached to gantry 40, provides surfaces angled with respect to the axis A so that the bearings 46, as shown in FIG. 2, provide both radial (directions perpendicular to the axis A) support and axial (directions parallel to the axis A) support.

As discussed in the background, the race 50 moves with constant angular velocity, but portions of the race 50 farther from the axis A have higher linear velocities than portions closer to the axis A while the gantry 24 is rotating. The bearings 46 are tapered into conical shapes to compensate for the linear velocity deviation. When the gantry 24 rotates, each bearing 46 in contact with the gantry 24 also rotates. Being conical in shape, the bearings each have a wide or larger diameter end and a narrow or smaller diameter end. Like the gantry, the surface at wide end of the bearing moves with a higher linear velocity than the surface at the narrow end. The bearings 46 are shaped with a varying diameter that is proportional to the slope and radial altitude of the race 50 such that there is no slippage between the bearings 46 and the race 50 as they all rotate.

Preferably, the bearings 46 are constructed of a metal core, preferably stainless steel, and coated with a polymeric coating, preferably polyurethane. The coating is preferably more than a surface coat, and more akin to a tire on a tricycle wheel, or the like. The coating is thick enough to provide for smooth cushioning, but thin enough that it stiffly supports the rotating gantry. Although polyurethane is preferred, other coatings that provide adequate stiffness (preventing axial and radial movement of the gantry 24) while preventing metal-to-metal contact between the race 50 and the bearings 46 are contemplated.

Figure 3:
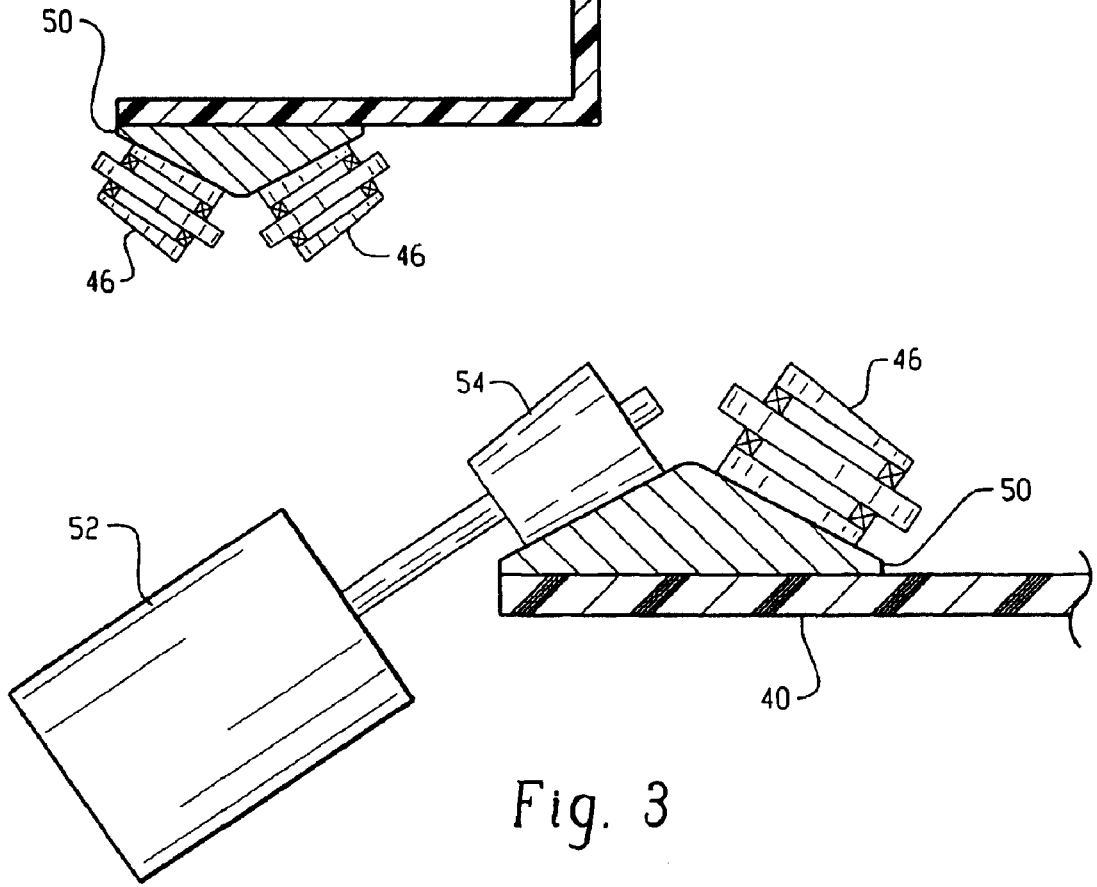
FIG. 3 is a detailed view of the roller bearings of FIG. 2 including a drive motor.

With reference to FIG. 3, one of the bearings is attached to an external drive motor 52 and becomes a drive bearing 54. The drive bearing 54 is coated with a substance that can be different from the other bearings 46 for improved friction with the bearing race 50. Such a substance may be a hardened rubber or the like.

Figure 4:
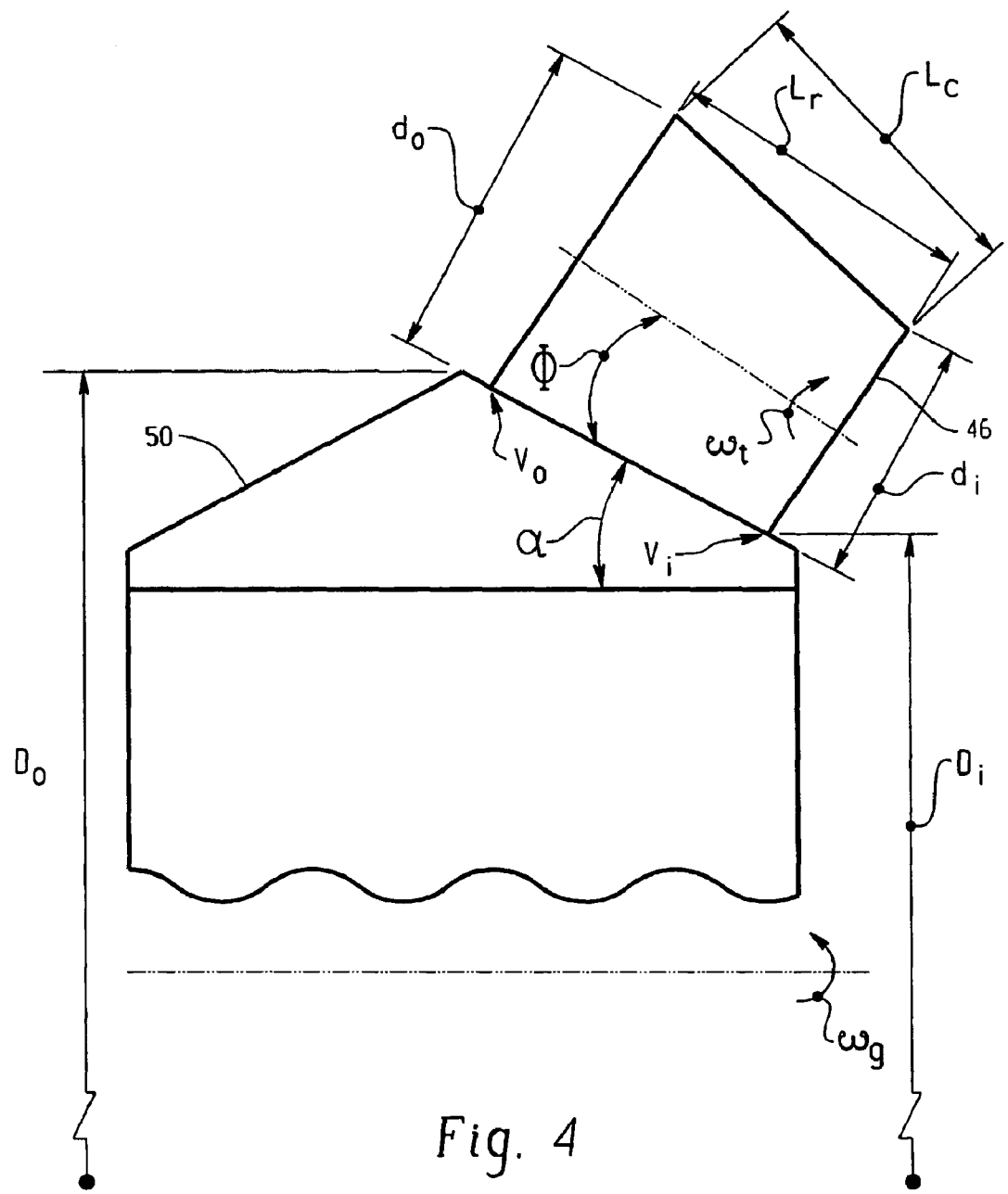
FIG. 4 is a geometrical representation of a bearing-race interface, in accordance with the present invention.

In order for the conical bearing race 50 and the tapered bearings 46 to be velocity matched, an angle of expansion that describes the growth of the diameter of a bearing 46 along the axle is found. With reference to FIG. 4, the angle φ is found to cause velocities $V_o$ and $V_i$ to match on both the race 50 and the bearings 46. First, a ratio of race 50 diameter to bearing diameter is found, $$R = \frac{D_o}{d_o}$$

where $D_o$ is the outer diameter of the race 50 and $d_o$ is the outer diameter of the bearing 46 and R is the ratio of the two measurements. It follows that the angular speed of the bearing $\omega_t$ is found by $$\omega_t = \omega_g R$$

where $\omega_g$ is the angular speed of the gantry in rpm. From geometry of the system it is known that $$L_c = \frac{D_o - D_i}{2\sin\alpha}$$

where $L_c$ is the length of the contact surface of the roller bearing 46, and $D_i$ is the inner diameter of the bearing race 50, and α is the angle of elevation of the bearing race 50. Solving for $D_i$, $$D_i = D_o - 2L_c \sin\alpha.$$

In order to velocity match the contact surfaces, the velocities $V_o$ and $V_i$ at the extremities of the bearing 46 and race 50 are found to match:

$$V_o = \omega_t \frac{d_o}{2} = \omega_g \frac{D_o}{2}.$$

Solving for $\omega_t$, $$\omega_t = \omega_g \frac{D_o}{d_o}$$

where $d_o$ is the outer diameter of the bearing 46. Similarly, $$\omega_t = \omega_g \frac{D_i}{d_i}$$

where $d_i$ is the inner diameter of the roller bearing 46. Combining the above two equations, it is found that $$d_i = d_o \frac{D_i}{D_o}.$$

Finally the angle φ can be found by:

$$\phi = \arcsin\left(\frac{d_o - d_1}{2L_c}\right).$$

The bearing axial length $L_r$ can be found by:

$$L_r = L_c \cos\phi$$

but it is to be understood that the actual length of the roller bearing 46 can vary to be slightly longer or shorter, keeping the same angle φ.

Figure 5:
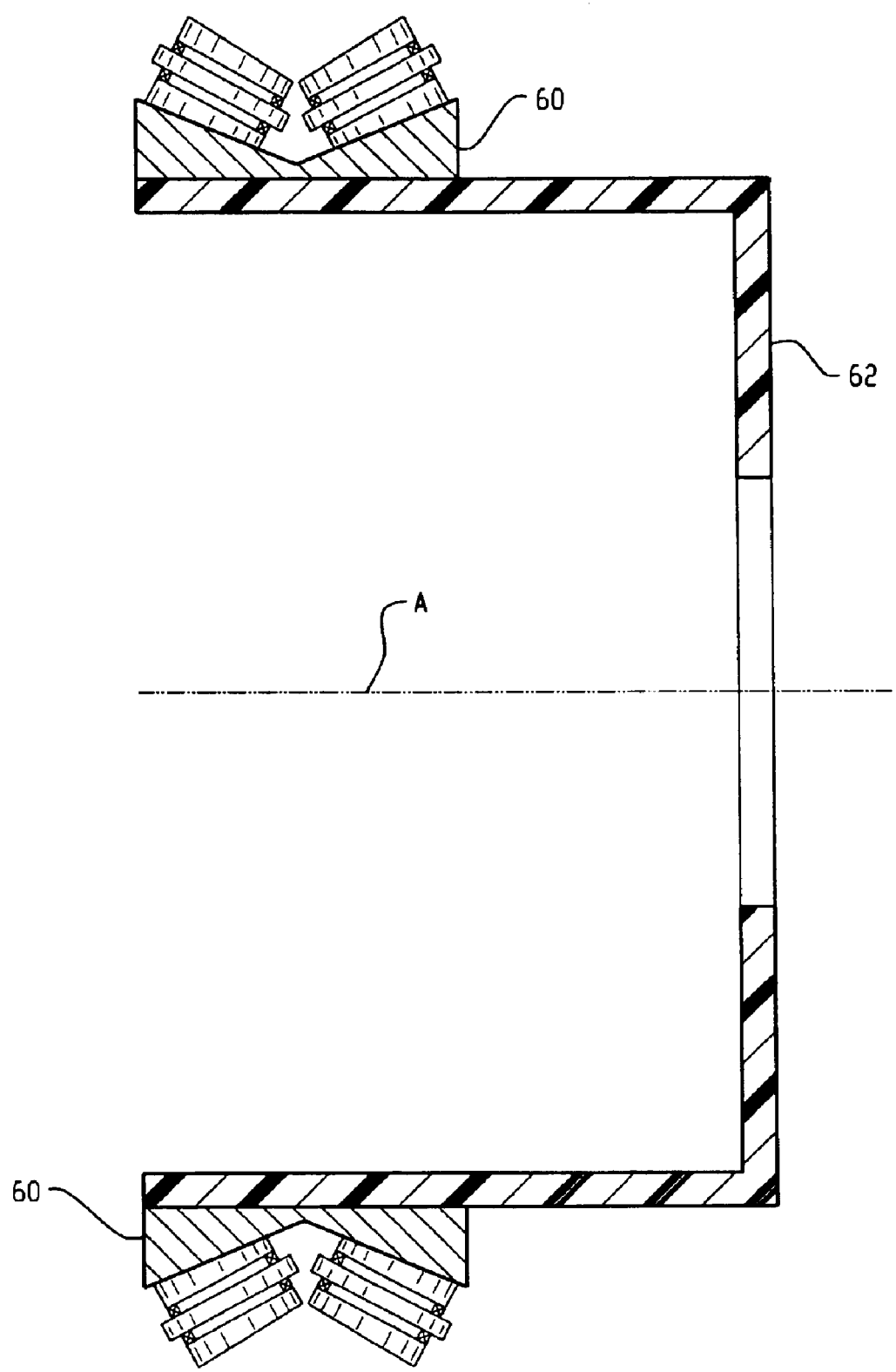
FIG. 5 is an alternate two-face race embodiment of the present invention.

In an alternate embodiment, and with reference to FIG. 5, a race 60 is an inverted negative of the race 50. This alternate race 60 still provides both axial and radial support for a gantry 62.

Figure 6:
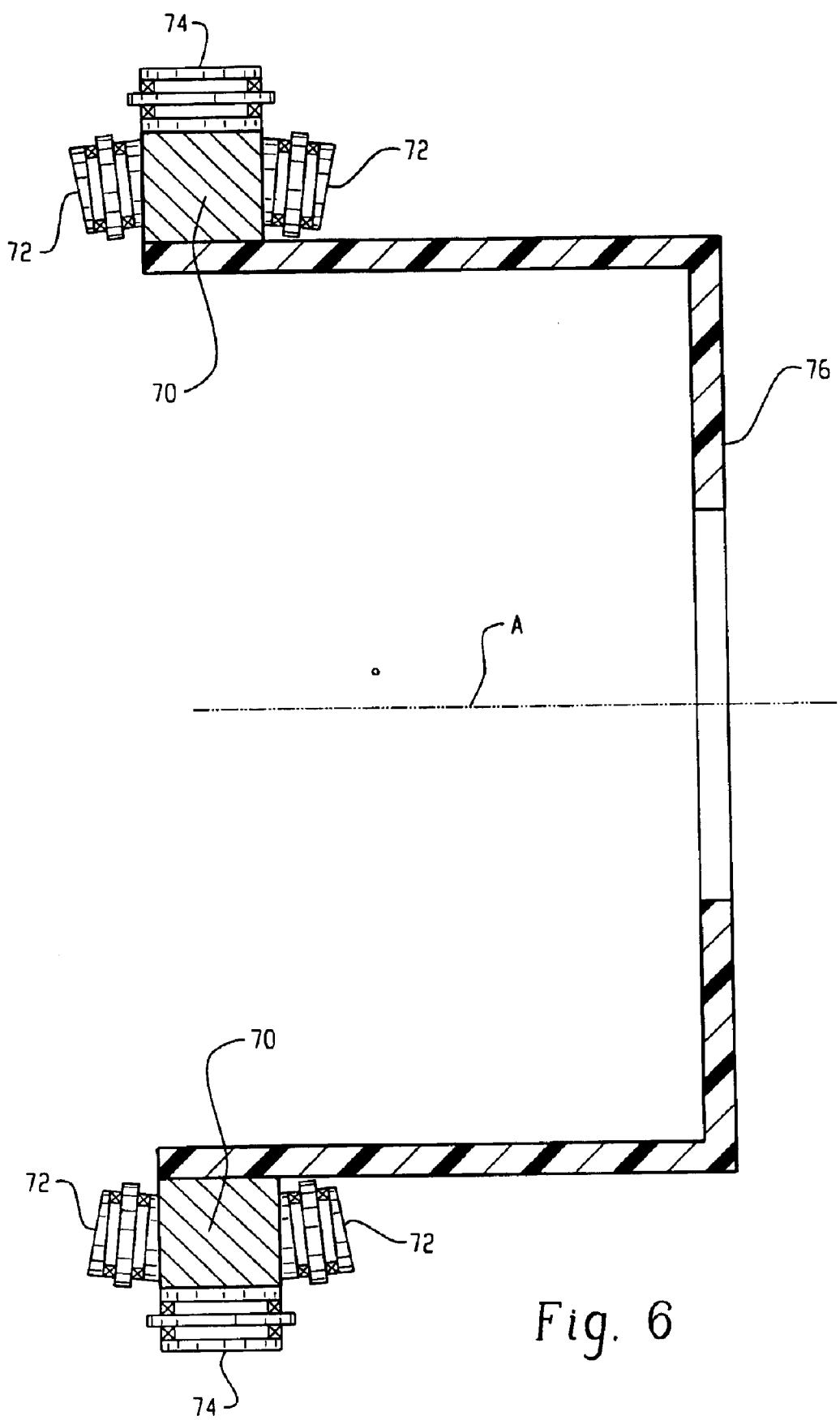
FIG. 6 is an alternate three-face race embodiment of the present invention.

In another alternate embodiment, and with reference to FIG. 6, a race 70 has three faces, tapered roller bearings 72 being adjacent the vertical sides of the race 70. A cylindrical (non-tapered) roller bearing 74 is adjacent the horizontal face of the race 70 since the entire face is equidistant from the axis A and thus does not display a velocity mismatch phenomenon. In this embodiment, the flat bearings 74 provide a gantry 76 with radial support, while the tapered roller bearings 72 provide the gantry 76 with axial support.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging device comprising:
   a first, stationary gantry;
   a second, rotating gantry having at least two bearing races, the second gantry rotating around a subject receiving region; and
   a plurality of tapered roller bearings for providing support to the rotating gantry to rotate around an axis of rotation;
   wherein the roller bearings have a taper angle φ defined by:

$$\phi = \arcsin\left(\frac{d_o - d_i}{2L_c}\right)$$

where $d_o$ is a large end diameter of the bearing, $d_i$ is a small end diameter of the bearing, and $L_c$ is a length measured along a surface of the bearing between the large and small ends.

2. The diagnostic imaging device as set forth in claim 1, further including:
   a radiation detector for detecting radiation from the subject receiving region;
   a reconstruction processor that reconstructs the received radiation into an image representation;
   a human readable display that converts the image representation into a human readable image.

3. The diagnostic imaging device as set forth in claim 2, further including:
   an x-ray source mounted on the rotating gantry to transmit x-rays through the subject receiving region.

4. The diagnostic imaging device as set forth in claim 1, wherein each tapered roller bearing has a truncated conical surface and rotates about a bearing axis, at a wide end, the conical surface moving with a higher linear velocity than at a narrow end.

5. The diagnostic imaging device as set forth in claim 1, wherein:
   surfaces of the at least two races move with varying linear velocities in accordance with distance from the rotation axis; and,
   surfaces of the tapered roller bearings rotate with varying linear velocities along a longitudinal axis of the bearing at the same angular velocity, the varying linear velocities of the tapered bearing surfaces being proportional to the varying linear velocities of the races.

6. The diagnostic imaging device as set forth in claim 1, wherein the tapered roller bearings provide at least axial support for the rotating gantry.

7. The diagnostic imaging device as set forth in claim 6, wherein the tapered roller bearings provide radial and axial support for the rotating gantry.

8. The diagnostic imaging device as set forth in claim 1, further including:
   at least one drive motor attached to one of the tapered roller bearings for driving the rotating gantry.

9. The diagnostic imaging device as set forth in claim 1, wherein the at least two races define a conical raceway on the rotating gantry.

10. The diagnostic imaging device as set forth in claim 1, wherein each roller bearing includes:
    an axle about which the bearing rotates;
    a metal core; and
    a polymeric coating on a contact surface of the bearing.

11. A method of diagnostic imaging comprising:
    supporting a rotating gantry, which surrounds a subject receiving region with a plurality of tapered roller bearings attached to a stationary gantry;
    rotating the gantry concurrently on the roller bearings, bearing races of the gantry contacting surfaces of the bearings; wherein
    a taper angle φ of the roller bearings by the relationship:

$$\phi = \arcsin\left(\frac{d_o - d_i}{2L_c}\right)$$

where $d_o$ is a larger end diameter of the bearing, $d_i$ is a smaller end diameter of the bearing, and $L_c$ is a length between the larger and smaller ends measured along a surface of the bearing.

12. The method as set forth in claim 11, further including:
    gathering data representative of radiation received from the subject receiving region;
    reconstructing the data into an electronic image representation; and
    converting the image representation into a human readable display.

13. The method as set forth in claim 12, further including:
    transmitting x-rays from a source mounted on the rotating gantry through the subject receiving region, the gathering step including detecting the x-rays that traversed the subject receiving region.

14. The method as set forth in claim 11, further including:
    rotating at least two bearing races with varying linear velocities in accordance with distance from the rotation axis; and,
    rotating surfaces of the tapered roller bearings with varying linear velocities along a longitudinal axis of the bearing at the same angular velocity, the varying linear velocities being proportional to the varying linear velocities of the races.

15. The method as set forth in claim 11, further including:
    providing at least axial support to the rotating gantry with the tapered roller bearings.

16. The method as set forth in claim 15, further including:
    providing radial and axial support for the rotating gantry with the bearings in a two bearing race system.

17. The method as set forth in claim 11, further including:
    covering a contact surface of the roller bearings with a polyurethane coating.

18. A roller bearing for use in conjunction with a computed tomography scanner, the roller bearing comprising:

a bearing race of a rotating gantry of the computed tomography scanner;

an axle about which the bearing rotates;

a tapered, conical body having a trapezoidal cross-section, the tapered surface of the body having a contact surface that interfaces with the bearing race of the rotating gantry of the computed tomography scanner, a taper angle $\phi$ of the bearing being defined by:

$$\phi = \arcsin\left(\frac{d_o - d_1}{2L_c}\right)$$

where $d_o$ is a larger end diameter of the bearing, $d_i$ is a smaller end diameter of the bearing, and $L_c$ is the length between the later and smaller ends measured along the contact surface of the bearing; and a polymeric coating on the contact surface of the bearing body.

* * * * *